United States Patent [19]
Kim

[11] Patent Number: 5,943,548
[45] Date of Patent: Aug. 24, 1999

[54] METHOD OF ANALYZING A WAFER IN A SEMICONDUCTOR DEVICE FABRICATION PROCESS

[75] Inventor: Dong-won Kim, Seoul, Rep. of Korea

[73] Assignee: Samsung Electronics Co., Ltd., Kyungki-do, Rep. of Korea

[21] Appl. No.: 08/842,271

[22] Filed: Apr. 24, 1997

[30] Foreign Application Priority Data

Jul. 2, 1996 [KR] Rep. of Korea ............... 96-26767

[51] Int. Cl.$^6$ .................... H01L 21/00; H01L 21/66; G01R 31/26
[52] U.S. Cl. ..................... 438/7; 438/16; 250/309
[58] Field of Search ................. 438/16, 7; 250/309

[56] References Cited

U.S. PATENT DOCUMENTS

| | | | |
|---|---|---|---|
| 3,742,227 | 6/1973 | Benninghoven | 250/282 |
| 4,874,946 | 10/1989 | Kazmerski | 250/309 |
| 5,086,227 | 2/1992 | Toita et al. | 250/309 |

*Primary Examiner*—Brian Dutton
*Attorney, Agent, or Firm*—Jones & Volentine, L.L.P.

[57] ABSTRACT

A method of analyzing a wafer in a semiconductor device fabrication process, includes the steps of: loading a wafer into a vacuum chamber where the vacuum pressure is maintained at a predetermined level; locating coordinates of a specific portion of the wafer and irradiating a primary ion beam onto the specific portion of the wafer at those coordinates; and detecting an impurity concentration by analyzing the mass of a specific ion from among secondary ions generated by collision of the primary ion beam with the surface of the specific portion of the wafer.

20 Claims, 2 Drawing Sheets

METHOD OF ANALYZING A WAFER IN A SEMICONDUCTOR DEVICE FABRICATION PROCESS

BACKGROUND OF THE INVENTION

1. Field of the Invention

The present invention relates to a method of analyzing a semiconductor device fabrication process. More particularly, the present invention is directed to a method of confirming the state of a process step by analyzing the concentration of an impurity in a wafer or in a layer formed thereon, or by analyzing the concentration profile of an ion or element injected into the wafer or a layer thereupon during the fabrication process.

2. Discussion of Related Art

Generally, a semiconductor device is fabricated in such a manner that many processes like photolithography and thin film formation are carried out on a wafer repeatedly. When these processes are performed, the state of the process is confirmed at all times by analyzing the concentration of an impurity in the wafer or in a layer formed on the wafer, or by analyzing the concentration profile of an ion or element injected into the wafer or layer. This analysis is conventionally performed through the process of Secondary Ion Mass Spectrometry(SIMS). As depicted in FIG. 1, a secondary ion mass spectrometer 1 carries out this process. The spectrometer 1 includes a vacuum chamber 2, primary ion generator 3, electrostatic magnetic field 4, mass analyzer 5 and detector 7.

A conventional method of analyzing an impurity concentration using the process of Secondary Ion Mass Spectrometry is explained using FIG. 2. One of the wafers 6 used in the fabrication process is selected. Then a specific portion of the selected wafer 6 is cut to a size of approximately 1 cm×1 cm. By doing so, a plurality of samples 6a are prepared. Before such a sample 6a is placed in the vacuum chamber 2 for analysis, it is placed in a subchamber (not shown) and the subchamber is evacuated in order to maintain a vacuum pressure of $10^{-6}$ to $10^{-7}$ torr. Thereafter, the sample 6a is placed in the vacuum chamber 2 of the secondary ion mass spectrometer 1, which always maintains a vacuum pressure of $10^{-9}$ to $10^{-10}$ torr.

Returning to FIG. 1, after the sample 6a is placed in vacuum chamber 2, primary ions are irradiated to the surface of sample 6a so as to generate secondary ions from the wafer or a layer formed on the wafer. For the secondary ions passing through the electrostatic magnetic field 4, only these secondary ions that have energy of a specific level can pass the electrostatic magnetic field 4. Calibration of the energy level and thus, measurement of the secondary ions is accomplished by controlling the intensity of the electrostatic magnetic field 4.

The mass of the specific secondary ions which pass the electrostatic magnetic field 4 is analyzed through mass analyzer 5 and detected by detector 7. By using this technique, it is possible to confirm the existence of a minute amount of an impurity contained in a wafer or a layer formed on the wafer, and to obtain a concentration profile for the depth of the impurity in the substrate or layer.

When the analysis for one sample 6a is completed, the sample 6a located in vacuum chamber 2 is moved to the subchamber(not shown), and the pressure of the subchamber is returned to the normal atmospheric level. Then, another sample 6a is analyzed by repeating the aforementioned procedure.

In conventional analysis methods using a secondary ion mass spectrometer or a similar analyzer, approximately five samples are taken from one wafer 6, and the same analysis procedure is carried out five times. Accordingly, more analysis time is required to handle all five samples, and the procedure is very complicated because the subchamber must be repeatedly pumped in order to maintain its vacuum at a predetermined level, and then the subchamber is discharged every time a sample 6a is replaced.

Since wafer 6 must be cut in order to form the sample 6a, the wafer 6 cannot be used in the production of the semiconductor devices. This results in additional costs due to the loss of production. Moreover, an accurate analysis is difficult to achieve because only one wafer is sampled and analyzed from among a large number of wafers. This is especially true since an accurate impurity profile even in one wafer may not be readily obtained. Accordingly, analysis reliability is poor.

SUMMARY OF THE INVENTION

Accordingly, the present invention is directed to a method of analyzing a semiconductor device fabrication process that substantially overcomes one or more of the limitations and disadvantages associated with the conventional art.

An object of the present invention is to provide a method of analyzing a semiconductor device fabrication process in which a specific portion of a wafer is directly analyzed using a pattern of measurement formed on the wafer, without formation of a separate sample, so as to shorten the analysis time and thereby improve the efficiency of the entire operation.

Another object of the present invention is to provide a method of analyzing a semiconductor device fabrication process in which every wafer is analyzed in order to carry out an accurate analysis and to improve the overall analysis reliability.

Still another object of the present invention is to provide an analysis system in which wafers used for analysis can be cleaned and then used in the production of semiconductor devices.

It is yet a further object of the present invention to provide a system in which the testing process can be performed automatically as part of the semiconductor fabrication process.

It is still an additional object of the present invention to reduce the overall stress to the semiconductor manufacturing and testing system by reducing the number of vacuum pumping operations required.

To achieve these and other advantages provided by the present invention, there is provided a method of analyzing a semiconductor device fabrication process, including the steps of: loading a wafer for analysis into a vacuum chamber, maintained at a predetermined level of vacuum pressure; locating coordinates for a first specific portion of the wafer to be used for analysis, and irradiating a primary ion beam onto the first specific portion at the coordinates; and detecting an impurity concentration for the first specific portion by analyzing a mass of a specific ion from among secondary ions generated by collision of the primary ion beam with the surface of the first specific portion of the wafer.

After the step of analyzing the first specific portion of the wafer, the method further includes the steps of relocating the coordinates and analyzing at least one other specific portion of the wafer.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate an embodiment of the invention, in which.

DETAILED DESCRIPTION OF PREFERRED EMBODIMENT

Figure 1:
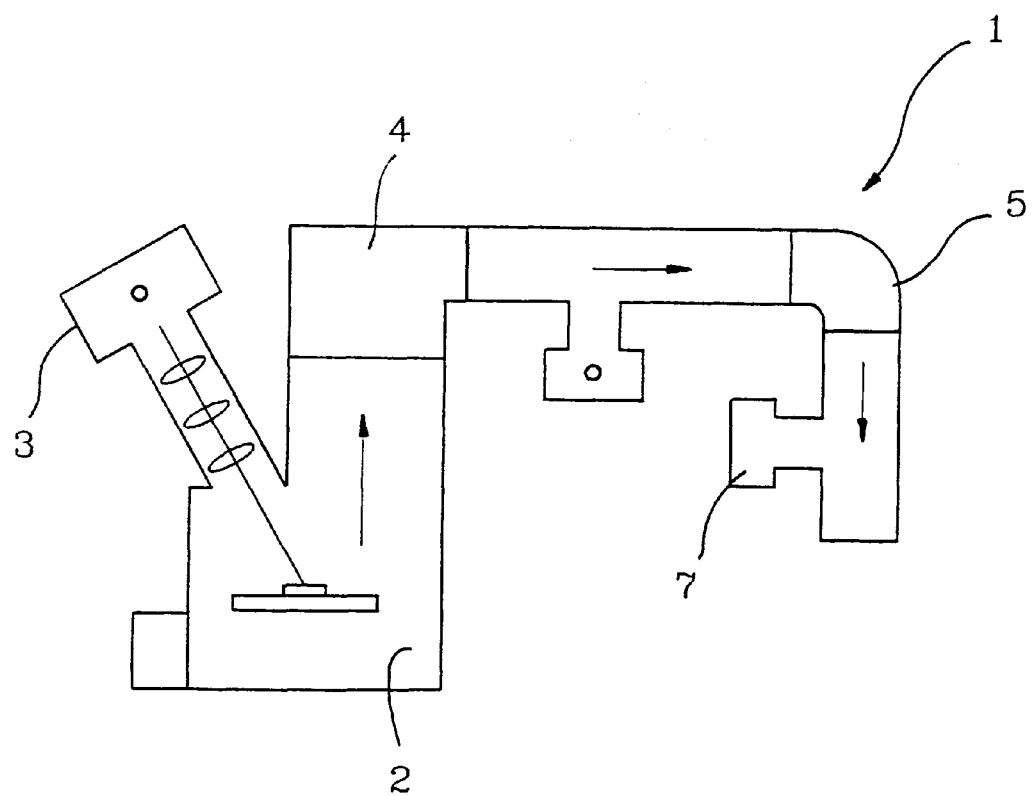
FIG. 1 depicts the configuration of a conventional secondary ion mass spectrometer.
Figure 2:
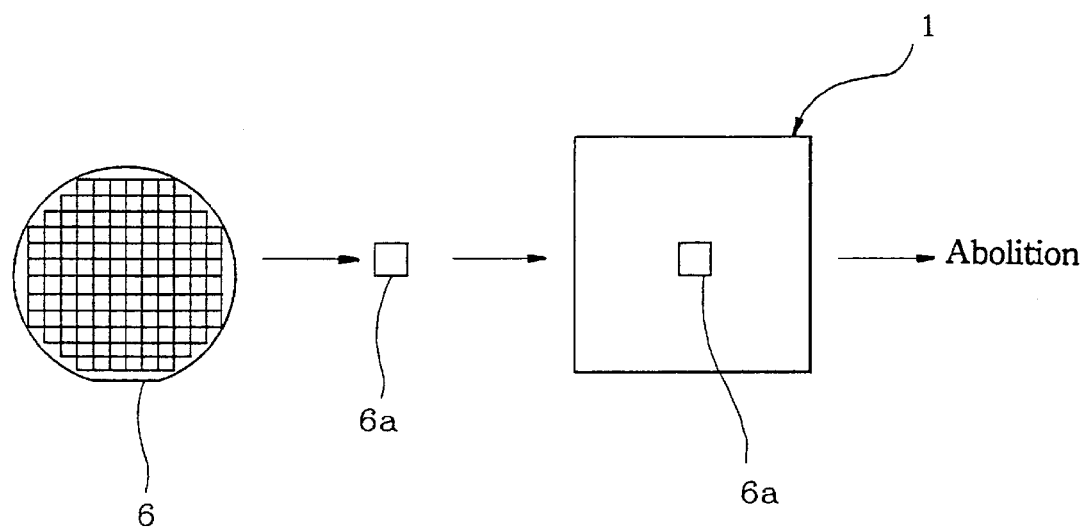
FIG. 2 depicts a conventional method of analyzing a semiconductor device fabrication process.
Figure 3:
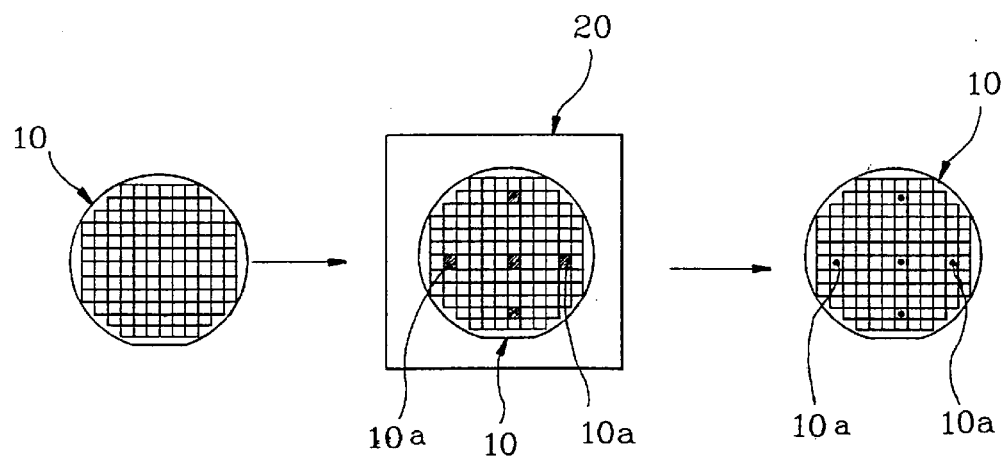
FIG. 3 depicts a method of analyzing a semiconductor device fabrication process according to the present invention.

FIG. 3 depicts a method of analyzing a semiconductor device fabrication process according to an embodiment of the present invention. The present invention employs a secondary ion mass analyzer 20 having a vacuum chamber which is capable of holding an entire wafer 10. The inner pressure of the vacuum chamber is maintained at $10^{-9}$ to $10^{-1}$ torr. Before wafer 10 is placed in the vacuum chamber of the secondary ion mass analyzer 20, it is placed in a subchamber (not shown) and the subchamber is pumped out in order to maintain its vacuum degree to $10^{-6}$ to $10^{-7}$ torr. Thereafter, the wafer 10 is moved into the vacuum chamber.

Coordinates are located on one of specific portions 10a of the wafer 10 located in the vacuum chamber of the secondary ion mass analyzer 20, and a primary ion beam is irradiated thereto. The impurity concentration of the wafer is determined by analyzing the mass of a specific ion among the secondary ions generated by collision of the primary ion beam and the specific portion 10a of the wafer using a conventional analysis method. It is preferable that the coordinates of the specific portion 10a are located by adjusting the beam irradiation direction of the primary ion generator while the wafer 10 is fixed. In an alternative embodiment, the coordinates may be located by moving the wafer 10 while the primary ion generator is fixed.

When the analysis for a specific portion 10a is completed, a second specific portion 10a is targeted by the selection of new coordinates, and then the analysis for the second specific portion is carried out using the aforementioned procedure. This procedure is repeated in order to sequentially analyze a plurality of specific portions 10a of the wafer. In a preferred embodiment, five portions of the wafer are subjected to targeting and analysis of secondary ion concentrations. However, the present invention is not limited thereto. Rather, the present invention can be practiced by analyzing a single specific portion 10a or any number of specific portions 10a deemed appropriate to the specific materials, process steps, layers placed on the wafer and the configuration of the ultimate device being manufactured.

In the analysis method of the present invention, the wafer 10 is placed directly into the vacuum chamber of the secondary ion mass analyzer 20, and then a plurality of specific portions 10a are sequentially analyzed. This is in contrast to conventional methods in which a plurality of samples taken from one wafer are analyzed separately and individually. Accordingly, analysis time decreases and operational efficiency is improved.

When the analysis for a specific portion 10a of wafer 10 is completed, that specific portion 10a cannot be used for semiconductor manufacture due to the destruction to that specific portion caused by the analysis. However, after the analysis, the wafer may be removed from the vacuum chamber, have its surface cleaned, and then subsequent semiconductor manufacturing processes may be carried out on the wafer. By doing so, the wafer can used to create a finished product. During the subsequent manufacturing process those specific portions 10a damaged by the analysis are identified and treated as faults.

Because the analysis method of the present invention does not damage the wafer as a whole, every wafer can be analyzed, sacrificing only specific portions 10a. Accordingly, an accurate analysis is obtained and analysis reliability is improved. When the analysis method of the present invention is carried out on-line with the fabrication process of the semiconductor device, it is possible to automatically analyze the impurity concentration of a specific layer after a specific process step is completed. If the concentration of the layer is determined to be normal, the next process step is performed.

In the above-described embodiment, the analysis is carried out using a secondary ion mass analyzer. However, the analysis method of the present invention may employ other devices similar to the secondary ion mass analyzer.

According to the present invention, the analysis procedure is simplified, and the entire wafer is not damaged, so that it can be used in the subsequent semiconductor fabrication process, thereby reducing the production costs. Moreover, the analysis method of the present invention can be used to monitor individual steps of the fabrication process when the analysis method is carried out on-line with the fabrication process.

It will be apparent to those skilled in the art that various modifications and variations can be made in the method of the present invention without departing from the spirit or scope of the invention. Thus, it is intended that the present invention should be considered to include any and all configurations, modifications, variations, combinations, equivalent arrangements or expansions falling within the scope of the following claims.

What is claimed is:

1. A method of analyzing a semiconductor device fabrication process, comprising:

loading a wafer for analysis into a vacuum chamber, maintained at a particular level of vacuum pressure;

locating coordinates for a first specific portion of the wafer to be used for analysis, and irradiating a primary ion beam onto the first specific portion at the coordinates;

detecting an impurity concentration for the first specific portion by analyzing a mass of a specific ion from among secondary ions generated by collision of the primary ion beam with the surface of the first specific portion of the wafer; and subjecting the wafer to subsequent fabrication processes, the subsequent manufacturing processes being performed after the analyzing of the first specific portion.

2. The method of analyzing a semiconductor device fabrication process as claimed in claim 1, wherein after the analyzing of the first specific portion of the wafer, the method further comprises:

relocating the coordinates to a second specific portion of the wafer; and performing the irradiating and the detecting on the second specific portion and analyzing a mass of a specific ion from among secondary ions generated by collision of the primary ion beam with the second specific portion of the wafer, the subsequent manufacturing processes being performed after the analyzing of the second specific portion.

3. The method of analyzing a semiconductor device fabrication process as claimed in claim 2, wherein after the analyzing of the second specific portion of the wafer, the method further comprises:

relocating the coordinates to a third specific portion of the wafer; and performing the irradiating and the detecting on the third specific portion and analyzing a mass of a specific ion from among secondary ions generated by collision of the primary ion beam with the third specific portion of the wafer, the subsequent manufacturing processes being performed after the analyzing of the third specific portion.

4. The method of analyzing a semiconductor device fabrication process as claimed in claim 1, wherein after the analyzing of the first specific portion of the wafer, the method further comprises:

sequentially relocating the coordinates to a plurality of other specific portions of the wafer; and sequentially performing the irradiating and the detecting on the other specific portions and analyzing a mass of a specific ion from among secondary ions generated by collision of the primary ion beam with the other specific portions of the wafer, the subsequent manufacturing processes being performed after the analyzing of the plurality of other specific portions.

5. The method of analyzing a semiconductor device fabrication process as claimed in claim 2, wherein the locating or relocating of the coordinates includes adjusting an irradiation direction of the primary ion beam while the wafer remains fixed.

6. The method of analyzing a semiconductor device fabrication process as claimed in claim 2, wherein the locating or relocating of the coordinates includes moving the wafer while the irradiation direction of the primary ion beam remains fixed.

7. The method of analyzing a semiconductor device fabrication process as claimed in claim 1, wherein the subsequent manufacturing processes comprise:

unloading the wafer from the vacuum chamber; and cleaning the surface of the wafer.

8. The method of analyzing a semiconductor device fabrication process as claimed in claim 2, wherein the subsequent manufacturing processes comprise:

unloading the wafer from the vacuum chamber; and cleaning the surface of the wafer.

9. The method of analyzing a semiconductor device fabrication process as claimed in claim 3, wherein the subsequent manufacturing processes comprise:

unloading the wafer from the vacuum chamber; and cleaning the surface of the wafer.

10. The method of analyzing a semiconductor device fabrication process as claimed in claim 4, wherein the subsequent manufacturing processes comprise:

unloading the wafer from the vacuum chamber; and cleaning the surface of the wafer.

11. A method of analyzing a semiconductor device fabrication process, comprising:

loading a wafer for analysis into a vacuum chamber, maintained at a particular level of vacuum pressure;

locating coordinates for a first specific portion of the wafer to be used for analysis, and irradiating a primary ion beam onto the first specific portion at the coordinates, the locating of the coordinates including moving the wafer while the irradiation direction of the primary ion beam remains fixed; and detecting an impurity concentration for the first specific portion by analyzing a mass of a specific ion from among secondary ions generated by collision of the primary ion beam with the surface of the first specific portion of the wafer.

12. The method of analyzing a semiconductor device fabrication process as claimed in claim 11, wherein after the analyzing of the first specific portion of the wafer, the method further comprises:

relocating the coordinates to a second specific portion of the wafer; and performing the irradiating and the detecting on the second specific portion and analyzing a mass of a specific ion from among secondary ions generated by collision of the primary ion beam with the second specific portion of the wafer.

13. The method of analyzing a semiconductor device fabrication process as claimed in claim 12, wherein the relocating of the coordinates includes moving the wafer while the irradiation direction of the primary ion beam remains fixed.

14. The method of analyzing a semiconductor device fabrication process as claimed in claim 12, wherein after the analyzing of the second specific portion of the wafer, the method further comprises:

relocating the coordinates to a third specific portion of the wafer; and performing the irradiating and the detecting on the third specific portion and analyzing a mass of a specific ion from among secondary ions generated by collision of the primary ion beam with the third specific portion of the wafer.

15. The method of analyzing a semiconductor device fabrication process as claimed in claim 11, wherein after the analyzing of the first specific portion of the wafer, the method further comprises:

sequentially relocating the coordinates to a plurality of other specific portions of the wafer; and sequentially performing the irradiating and the detecting on the other specific portions and analyzing a mass of a specific ion from among secondary ions generated by collision of the primary ion beam with the other specific portions of the wafer.

16. The method of analyzing a semiconductor device fabrication process as claimed in claim 15, wherein the relocating of the coordinates includes moving the wafer while the irradiation direction of the primary ion beam remains fixed.

17. A method of analyzing a semiconductor device fabrication process, comprising:

loading a wafer for analysis into a vacuum chamber, maintained at a particular level of vacuum pressure;

locating coordinates for a specific portion of the wafer to be used for analysis, and irradiating a primary ion beam onto the specific portion at the coordinates;

detecting an impurity concentration for the specific portion by analyzing a mass of a specific ion from among secondary ions generated by collision of the primary ion beam with the surface of the specific portion of the wafer, not all portions of the wafer being subjected to the irradiating.

18. The method of analyzing a semiconductor device fabrication process as claimed in claim 15, further comprising subjecting the wafer to subsequent fabrication processes, the subsequent manufacturing processes being performed after the analyzing of the specific portion.

19. The method of analyzing a semiconductor device fabrication process as claimed in claim 17, wherein the locating of the coordinates includes moving the wafer while the irradiation direction of the primary ion beam remains fixed.

20. The method of analyzing a semiconductor device fabrication process as claimed in claim 17, wherein after the analyzing of the specific portion of the wafer, the method further comprises:

sequentially relocating the coordinates to at least one other specific portion of the wafer; and sequentially performing the irradiating and the detecting on the at least one other specific portion and analyzing a mass of a specific ion from among secondary ions generated by collision of the primary ion beam with the at least one other specific portion of the wafer.

* * * * *